United States Patent [19]

United States Patent [19]
Distl et al.

[11] Patent Number: 4,822,169
[45] Date of Patent: Apr. 18, 1989

[54] MEASURING ASSEMBLY FOR ANALYZING ELECTROMAGNETIC RADIATION

[76] Inventors: Richard Distl, Edlingerstrasse 7, D-8000 München 90; Ulrich Schmidt, Kasinostrasse 54, D-5100 Aachen, both of Fed. Rep. of Germany

[21] Appl. No.: 878,877
[22] PCT Filed: Sep. 25, 1985
[86] PCT No.: PCT/EP85/00498
 § 371 Date: Jul. 22, 1986
 § 102(e) Date: Jul. 22, 1986
[87] PCT Pub. No.: WO86/02159
 PCT Pub. Date: Apr. 10, 1986

[30] Foreign Application Priority Data
 Sep. 25, 1984 [DE] Fed. Rep. of Germany ....... 3435189
 Jan. 7, 1985 [DE] Fed. Rep. of Germany ....... 3500307

[51] Int. Cl.$^4$ .......................... G01J 4/04; G01N 22/21
[52] U.S. Cl. ............................................. 356/364
[58] Field of Search ............... 356/364, 365, 366, 367, 356/368

[56] References Cited

U.S. PATENT DOCUMENTS

| | | | |
|---|---|---|---|
| 2,718,170 | 9/1955 | Lyot | 356/365 |
| 3,034,395 | 5/1962 | Zandman | 356/34 |
| 3,183,763 | 5/1965 | Koester | . |
| 3,481,671 | 12/1969 | West et al. | . |
| 3,771,874 | 11/1973 | Sadjian | 356/365 |
| 3,871,771 | 3/1975 | Scott | 356/364 |
| 3,927,945 | 12/1975 | Bates | 356/366 |
| 4,272,195 | 6/1981 | Kaye | 356/368 |
| 4,400,062 | 8/1983 | Mori et al. | 356/365 |

FOREIGN PATENT DOCUMENTS

| | | | |
|---|---|---|---|
| 0115819 | 6/1985 | Japan | 356/368 |
| 1135407 | 7/1966 | United Kingdom | 356/364 |

Primary Examiner—Richard A. Rosenberger
Attorney, Agent, or Firm—Paul L. Sjoquist

[57] ABSTRACT

The measuring assembly for analyzing electromagnetic radiation comprises the following structural groups arranged one behind the other in the beam path:
 at least one linear polarizer (2);
 at least one optically active element (3) of known optical activity, i.e. known frequency response of the rotation of the polarization plane; and
 at least one analyzer (4) the polarization direction of which has a fixedly set orientation with respect to the direction of transmission of the linear polarizer. The beam issuing from the analyzer (4) is passed through a photosensitive sensor (7,8) to a measuring circuit. The total intensity of the radiation under investigation is determined in various ways by forming a reference signal, namely by direct measurement with the optically active element temporarily removed from the beam path, by neutralizing a partial beam, or by a beam splitting analyzer. The measuring assembly permits very rapid analysis (up to real time measurement) of electromagnetic radiation at an extremely high resolution without requiring any mechanically movable parts. Fields of application of the measuring assembly are the determination of the optical center of gravity of the radiation, the determination of the spectral characteristic of the radiation, as well as spectrometric and/or photometric examinations of samples.

13 Claims, 6 Drawing Sheets

MEASURING ASSEMBLY FOR ANALYZING ELECTROMAGNETIC RADIATION

TECHNICAL FIELD

The invention relates to a measuring assembly for analyzing electromagnetic radiation.

Important fields of application of the measuring assembly designed in accordance with the invention are:
(a) The determination of the optical center of gravity of electromagnetic radiation,
(b) the determination of the spectral characteristic of electromagnetic radiation,
(c) spectrometric and/or photometric examinations of samples.

STATE OF THE ART

The measurement of the wavelength of light is the basis of a great number of physical examinations, for instance in spectroscopy of photometry. Another field of application of the measurement of wavelengths is the quality control in the technical field, e.g. the measurement of the center of gravity wavelength of semiconductor lasers.

Usually so-called monochromators are used for this purpose. They permit only light of a certain wavelength to pass in response to the position of a diffraction grating at an outlet slit. Such instruments are of very complicated structure in order to obtain the necessary resolution of the result of measurement. Furthermore, this operating principle does not permit the analysis of light at quickly varying wavelength or short-term pulses because the balancing time for positioning the diffraction grating is rather long. Consequently measurement values cannot be detected in real time. With conventional monochromators another disadvantage resides in the fact that, apart from other parameters, the resolution in the first place is determined by the width of the outlet slit. If high resolution is to be obtained, long paths within the monochromators and small slit widths are required, and this again involves high losses in intensity. In the analysis of weak signals which, among others, are the rule in the Raman spectroscopy, therefore, monochromators are useful with limitations only, e.g. by putting up with long integration times. As monochromators because of their principle, furthermore integrate across the spectral band width passing the outlet slit, as regards the intensity, the determination proper of the energy content of the radiation to be analyzed is impossible, and yet this would be required in many areas of chemical and physical elucidation of structures.

In numerous fields of application in research and technical quality control the radiation to be examined is available only in the form of pulses of short duration. As an example in this respect the manufacture and use of pulse semiconductor lasers and solid body lasers may be mentioned. In chemical analysis, moreover, it is observed that increasing use is being made, in the optical analysis, of radiation sources which emit shorter light pulses. Among others this has the advantage that the sample is treated with care and, at the same time, higher optical outputs are available. Monochromators usually are not suitable in this case for determining the wavelength or evaluating the spectral characteristic because, as explained above, the dispersing element cannot cover the entire spectrum within the short pulse duration because of the balancing principle.

Often serious problems are encountered in all fields of chemical and physical analyses making use of the means of spectroscopy of photometry if substances are to be identified selectively which have very similar emission or absorption spectra. The reason is that with such measuring tasks the outlet slit of the monochromator provided in the customary spectrometers would have to be infinitely small if the necessary resolution is to be reached for differentiating between substances having very similar spectra. A reduction of the outlet slit, however, involves the great disadvantage of considerably lowering the sensitivity of the measuring system. Thus the outlet slit cannot be reduced at random. Rather, conventional spectrophotometers are dependent on the substances contained in mixtures to be analyzed having characteristics peaks based on which the substances are easily identified. The problems described are touched on, for instance, in the application print DE-AS 24 30 011 "Zweistrahl-Photometer mit Iterferenzfilter". For examining coherent light, there are so-called wavemeters which determine the wavelength based on interferometric measurements by means of a reference laser. This method, too, is very expensive and too slow for many applications.

It has been known for a long time that the optical activity also is a function of the wavelength of the light passing through the optically active substance. This is designated "optical rotation dispersion" (ORD) (cf. e.g. "Zeitschrift für Instrumentenkunde", 75th year, 1967, pp. 111-124). Every optically active substance has its own characteristic ORD spectrum. This is very well known in science for many optically active substances, such as quartz.

The characteristic described above has been utilized for years at the Physikalisch-Technische Bundesanstalt of Braunschweig for very exact measurements of the wavelength (cf. also "Zeitschrift fur angewandte Physik", 20th vol., no. 5, 1966, pp. 419 to 423). Here a circular polarimeter is used to determine the rotation caused by a quartz block, 50 mm long, of light which was previously polarized linearly (cf. e.g. "Aufgabenbericht PTB", Labor fur Polarimetrie). This measuring method which has been known for a long time requires intensive use of instruments for higher resolutions and also is very slow because of the balancing principle of the circular polarimeter.

In principle, however, very good measuring accuracy is obtainable by determining the wavelength by way of the ORD of the optical activity. In applying this principle, moreover, the optical activity always is integrated across the band width so that the result of measurement directly provides the center of gravity wavelength. In many cases of application the determination of this magnitude is of considerable importance. And yet the problems in the measuring technique have prevented any widespread use of this measuring principle.

A multibeam measuring assembly for the polarimetric examination of samples in a real time method not including the disadvantage of slow balancing of a circular polarimeter has been described in the PCT application PCT/EP84/00050 (SCHMIDT, DISTL). The teaching of this PCT/EP84/00050 among others is based on the fact that the direction of oscillation of the light beam may be calculated by a determination of the ratio of the relative intensity of the light beam to be analyzed downstream of an analyzer and the absolute intensity thereof upstream of the analyzer. Here the light beam having passed the sample is split by a beam splitter, preferably a diffraction grating into a reference beam and at least one examining beam in the beam path of which an analyzer is positioned which has a fixed transmission direction. The intensities of the partial beams are detected by associated photosensitive sensors. The signal outputs of the photosensitive sensors are connected to the inputs of a measuring circuit for determining polarimetric magnitudes which can be coordinated with the sample.

This measuring circuit substantially has the following structure: A short time storage connected downstream of each photosensitive sensor stores the output signals of the photosensitive sensors in synchronism and for a short period. A control circuit associated with the short time storages takes over control of the short time storages. The formation of the ratio between relative intensity and absolute intensity is effected by a divider circuit which operates without delay and is connected at the input end to the outputs of the short time storages. A digital data processing means connected at its input end to the output of the divider circuit is provided for the calculation and output of the optical activity to be assigned to the sample. The measuring circuit further comprises at least one A/D converter to convert the analog signals into digital ones for the further processing.

In the multibeam measuring assembly mentioned above the mode of operation of the beam splitter is of decisive significance regarding the measuring accuracy. Dielectric beam splitters, for example, are not suitable because their splitting ratio if a function of the oscillation direction of the impinging light beam. Therefore, also the falsifying mode of this beam splitter enters into the measuring result. The above mentioned PCT/EP84/00050 suggests to use a diffraction grating as the beam splitting element. In this respect it is important above all that the light beam impinging on the diffraction grating always is incident in the same manner on the grating structure as the efficiency of diffraction is a function of the angle of incidence. Thus it must be aimed at giving the radiation source the best possible approximation of a point and this cannot be obtained without expensive guidance of the beam path. It is another disadvantage that this measure involves corresponding light losses. As the direction of oscillation of the reference beam is not defined, moreover, the vector sensitivity of the photosensitive sensor associated with the reference beam distorts the measuring result.

It is not possible to use the above mentioned multibeam measuring assembly for measuring the oscillation direction of electromagnetic radiation at variable wavelength because the angle of diffraction at the grating depends on the wavelength so that the detectors cannot be assigned a fixed position.

DISCLOSURE OF THE INVENTION

It is therefore an object of the invention to improve the measuring assembly of the kind mentioned above such that rapid measurements (up to real time) become possible at the highest possible measuring accuracy and good resolution, the greatest possible dynamic range of the intensity of the radiation to be examined being covered.

The measuring method applied with the invention among others is based on the exploitation of the optical rotation dispersion of optically active substances. In this context the direction of oscillation of previously linearly polarized radiation is determined after it has passed an optically active element. The measuring values thus obtained together with the known ORD spectrum of the optically active substance may be used to determine the center of gravity wavelength of the electromagnetic radiation. As no moving parts are required in principle in the course of measurements, these measurements may be made in real time.

The subject matter of the invention as explained is especially well suited for determining the center of gravity wavelength of monochromatic radiation, for example as tuning control in pigment or solid body lasers. Moreover, such a measuring assembly also may be used for investigating light pulses of very short duration, e.g. of semiconductor pulse lasers as to their wavelength and energy content. Furthermore, the integrating effect of the optically active element opens entirely new possibilities of pure substance characterization and mixture analysis in the field of spectral analyses like the photometry. In accordance with a specific embodiment of the invention such analyses practically may be made in real time.

The electromagnetic radiation to be analyzed is translated by a linear polarizer into linearly polarized radiation, then passes an optically active element of known optical activity and finally impinges on at least one analyzer. Upstream of the output of the analyzer a means is provided for determining a reference signal which is proportional to the absolute intensity. The radiation transmitted by the analyzer is detected by a first photosensitive sensor. Further the reference beam obtained by the means just mentioned is incident on a second photosensitive sensor. For further processing of the electrical signals thus obtained, the outputs of the photosensitive sensors finally are connected to the inputs of a measuring circuit.

The teaching of the invention starts from the principle described in the PCT application PCT/EP84/00050 to determine the direction of oscillation of the radiation incident on the analyzer and subsequently to determine the center of gravity wavelength. The principle mentioned provides for determining the direction of oscillation of linearly polarized light by a determination of the ratio between the relative intensity of the light to be analyzed downstream of an analyzer and the absolute intensity upstream of the analyzer and subsequent calculation.

The following relationship also called Malus' law may be applied for computing the intensity on a real analyzer:

$$A = A_0 \cdot \cos^2 \cdot C$$

wherein:
- A: Intensity downstream of the analyzer
- $A_0$: Intensity upstream of the analyzer
- $\alpha$: Angle between incident linearly polarized radiation and direction of transmission of the analyzer
- C: Constant factor caused by reflection losses on entry and exit of the radiation as well as absorption of the analyzer material.

Resolving the above formula according to $\alpha$, the following relation may be drawn up:

$$\alpha = \arccos \sqrt{\frac{A}{A_0 \cdot C}}$$

Now the measuring circuit is applied to determine the ratio of $A/A_oC$ and this is applied to the digital data processing means for further processing.

In a preferred modification of the invention the analyzer and the means determining the reference signal are combined in a polarizing beam splitter, referred to below as beam splitting analyzer.

None of the partial beams may be associated directly with a reference value (corresponding to the absolute intensity) in a polarizing beam splitter. The starting basis of the teaching according to the invention is that the light energy impinging on the beam splitting analyzer, in other words the reference value may be determined, for example, by the following relation:

$$C \cdot A_o = E_o + E_a$$

wherein:
- $A_o$ = Energy of the light upstream of the beam splitting analyzer
- $E_o$: Energy of the ordinary partial beam
- $E_a$: Energy of the extraordinary partial beam
- $C$: Constant factor The intensities of both partial beams are detected by respective photosensitive sensors associated with them. Preferably each photosensitive sensor is followed by a short time storage in order to obtain the same measuring conditions and thus an improvement of the measuring accuracy on the whole. In an especially preferred modification the short time shortages are sample/hold circuits. A first control circuit associated with the short time storages warrants synchronous control, i.e. holding of the intensities at exactly the same time.

In accordance with the relationship described above, an adder circuit connected downstream of the short time storages is used to determine, first of all, the sum of $E_o$ and $E_a$. The output value of the adder circuit thus is directly proportional to the energy of the light in front of the beam splitting analyzer. Subsequently a divider circuit connected at the input end to the output of the adder circuit and the the output of one of the short time storages is used to determine the relationship of the intensity of the partial beam associated with the respective short time storage, i.e. the relative intensity to the output value of the adder circuit, i.e. the absolute intensity. The standardized value thus determined then is digitalized by an A/D converter and applied to the digital data processing means for further evaluation, i.e. calculation of the rotary value $\alpha$. The following relationship exists between the rotary value $\alpha$ determined in the measuring assembly described above and the specific optical activity of the optically active element:

I. For optically active substances dissolved in optically inactive solvents:

$$[\alpha] = \frac{\alpha \cdot 100}{C \cdot L}$$

wherein:
- $\alpha$: = rotary value measured
- $C$: = concentration of the optically active substance
- $L$: = layer length passed II. For optically active solids:

$$[\alpha] = \frac{\alpha}{L}$$

The values $C$ and $L$ are called from a memory which is connected to the digital data processing means.

The optical rotation dispersion (ORD) spectrum of an optically active substance, i.e. the dependence of the optical activity on the wavelength is an invariable characteristic of this substance and is defined by:

$$f(\lambda) = [\alpha]_\lambda$$

The inverse function of ORD is represented as follows:

$$\lambda = f([\alpha])$$

In accordance with the invention a memory is connected to the digital data processing means to permit a comparison between the rotation determined of the polarization plane and the ORD spectrum of the optically active element, the memory also storing the inverse function of the ORD, for instance in the form of a table.

The selection of a suitable optically active element substantially is determined by the required wavelength measuring range and the desired resolution. For instance, there is a great number of optically active substances which have a very steeply rising or falling ORD in the vicinity of resonance points so that at these points extremely high resolutions of measured values can be obtained. By contrast, crystal quartz, for example, offers uniform accuracy over a wide measuring range. In a preferred embodiment of the wavelength measuring assembly according to the invention the optically active elements consist of correspondingly cut quartz crystal plates. The ORD spectrum of quartz follows the normal Cotton effect, and the characteristic thereof is well known from the field of polarimetry in which it is used as a gauging standard (cf. Icumsa Proceedings, 17th Session, Montreal 1978).

In view of the strict requirements regarding the measuring accuracy, in general, beam splitting crystal polarizers, such as Foster beam splitters are used as the beam splitting analyzers. The separation of the radiation components which are polarized orthogonally with respect to one another thus is made on the basis of the different optical densities of the partial beams in the polarizer medium. The use of a beam splitting analyzer for generating the reference signal specifically has the advantage that the spectral absorption of the optically active element does not influence the result of the measurement.

In a special modification of the measuring assembly according to the invention a high degree of polarization also may be obtained by, for example, arranging in series less expensive polarizing dielectric beam splitting cubes of inherent low cancelling capacity. Thus the beam portion transmitted may be polarized to any desired extent. The intensity value $E_o$ associated with the ordinary partial beam is determined by means of an adder circuit which sums the intensities of all reflected components of the beam splitting cubes. The signal output of the photosensitive sensor associated with the transmitted partial beam of the last polarizing beam splitter is connected directly with the input of one short time storage. The input of the other short time storage, on the other hand, is connected to the output of the summing circuit. The output signals of both short time storages then are treated in the same manner as in the measuring circuit represented initially.

In accordance with another modification of the invention the magnitude $A_o$ also may be determined by providing a means in the beam path in front of the analyzer suitable to neutralize part of the radiation to be analyzed in the beam path. This means preferably is a beam splitter having a defined neutralizing factor, such as a metallic or dielectric beam splitter. A photosensitive sensor, acting as a detector, is provided in one of the partial beams of the beam splitter to determine the reference signal.

In an especially preferred embodiment the beam splitter is disposed in front of the linear polarizer. However, the beam splitter also may be disposed downstream of the polarizer, or its function may be combined with that of the linear polarizer in the form of a polarizing beam splitter. If the means mentioned is located between the optically active element and the analyzer it must not vary the polarization properties of the transmitting radiation in undefined manner because otherwise the subsequent analyzer would be useless. A number of further methods are available for generating a reference signal, e.g. by introducing a mirror temporarily into the beam path or by pivoting at least one of the polarizer means or the optically active element cyclically out of the beam path.

In accordance with the assembly described above a reference beam is balanced or neutralized directly out of the beam path. The photosensitive sensor associated with this partial beam supplies an output signal which consequently is directly proportional to the absolute intensity upstream of the analyzer. Thus the adder circuit required in the measuring assembly described initially may be dispensed with which was used to sum the intensities of the partial beams issuing from the beam splitting analyzer to form a reference value. The signal outputs of the short time storages associated with the photosensitive sensors now are connected directly to the inputs of the divider circuit. The further processing of the measuring signals is carried out in a manner analogous to what has been described with reference to the measuring assembly presented initially.

If the transmitting direction of the linear polarizer is parallel to the transmitting direction of the analyzer, the rotation of the oscillation direction of light caused by the optically active element may amount to a maximum of 90 degrees in order to exclude ambiguities in the measurement result. As the optical activity is proportional to the layer length passed, the latter thus must be so selected that the rotation induced in the necessary measuring range does not exceed 90 degrees.

The total resolution of the measuring system, i.e. the wavelength is determined by the differential $d\lambda/d\alpha$ together with the resolution of $\alpha$. This shows that either little resolution at a great measuring range or high resolution at a small measuring range with a great layer length may be obtained.

In some cases of application an especially great measuring range together with high resolution may be required. As explained, the layer length passed of the optically active element must be eather great in order to obtain high resolution. Accordingly the rotation of the plane of oscillation caused by the optically active element may exceed 90 degrees at a predetermined measuring range.

Then the following relation exists between the rotary value measured and the actual rotary value:

wherein:
$\alpha = \phi + k \cdot 90$ degrees
$k := $ an integer
$\alpha := $ actual rotary value
$\phi := $ measured rotary value The variable k may be determined, for instance, by balancing another beam out of the electromagnetic radiation to be analyzed by use of a beam splitter. This beam subsequently is converted into linearly polarized radiation by use of a linear polarizer, then passes through an optically active substance and, finally, likewise impinges on an analyzer. The measuring assembly finally comprises at least one means to generate a reference signal. The measuring assembly also is designated for processing the output signals of the photosensitive sensors arranged in the second beam path. From the point of view of the measuring technique, therefore, both beam paths are treated equally.

The optically active substances associated with the two beam paths have different optical activities, in other words, at the same specific optical activity their layer lengths are different. The beam referred to subsequently as measuring beam and passing through the optically active element which has the greater layer length and consequently the higher resolution serves for determination of the measuring value proper. The other beam referred to below as measuring range beam and passing through the optically active element of the smaller layer length and consequently less resolution substantially serves for determining the wavelength range.

As the layer length passed and the rotation of the plane of oscillation thus caused are proportional with respect to each other, the following relation applies:

$$\alpha_1/s_1 = \alpha_2/s_2$$

wherein:
$\alpha_1 := $ actual rotary value at layer length $s_1$
$\alpha_2 := $ actual rotary value at layer length $s_2$
$s_1 := $ layer length passed of the measuring beam
$s_2 := $ layer length passed of the measuring range beam If both equations are linked, the following formula is obtained:

$$(\phi_1 + k_1 \cdot 90 \text{ degrees}) \cdot s_1 = (\phi_2 + k_2 \cdot 90 \text{ degrees}) \cdot s_1$$

If the layer length of the optically active element associated with the measuring range beam is so selected that the rotary value does not exceed 90 degrees across the measuring range required, then it is possible to assume $k_2 = 0$. The result thus obtained is:

$$\phi_2 = s_2/s_1 \cdot (\phi_1 + k_1 \cdot 90 \text{ degrees})$$

Restructuring of the above formula further provides:

$$k_1 \cdot 90 \text{ degrees} = \phi_2 s_1/s_2 - \phi_1$$

By reinserting the relation thus obtained into the general formula mentioned above, finally, the result is:

$$\alpha_1 = \phi_1 + INT\left(\frac{\phi_2 s_1/s_2 - \phi_1}{90 \text{ degrees}}\right) \cdot 90 \text{ degrees}$$

The center of gravity wavelength of the electromagnetic radiation to be analyzed then is determined, as described above, by means of the ORD spectrum based on the rotary value $\alpha_1$ which was thus established at greater accuracy. The determination of $\phi_2$, i.e. the rotary value measured in the measuring range beam path need not be carried out at the same degree of accuracy as the determination of $\phi_1$ because of the INT function (integer). Thus the structural elements associated with the measuring range beam path may be selected to be of much less accuracy.

In a specific modification of the invention each short time storage is preceded by an amplifier of programmable amplification. For this purpose it is preferred to use so-called instrument amplifiers with which the resistance determining the amplification is variable by a resistor and switch network. The switch networks are controlled by a second control circuit. Different intensities of the electromagnetic radiation to be analyzed thus may be balanced in certain steps which are fixed by the resistance values in the resistor network.

The advantage obtained resides in the fact that only the analog components upstream of the instrument amplifier, i.e. the photosensitive sensors and their input operation amplifiers must meet the requirements of the desired resolution and accuracy, multiplied by the necessary dynamic range which is given by different intensities of the electromagnetic radiation to be analyzed. All analog components following the instrument amplifier, on the other hand, only must come up to the desired measuring accuracy. If for instance a resolution and accuracy of the result of measurement of 0.01 radians is required and if radiations are to be examined whose intensities may vary by a factor of 100, the analog components following the instrument amplifier may have a maximum non-linearity of 15 ppm, while those upstream of the instrument amplifier may have a non-linearity of 0.15 ppm. This circumstance is of considerable significance because practically there are no sample/hold circuits (here used as short time storages) which do have an accuracy of 0.15 ppm. Without the measuring assembly according to the invention including the programmable instrument amplifier, therefore, a considerable deterioration of the measuring accuracy would have to be put up with at least at low radiation intensities. However, it should be emphasized in this context that the instrument amplifiers of programmable amplification are required only for the purpose of obtaining optimum control of subsequent analog structural elements with the aim of maintaining their properties of linearity at low radiation intensities. By virtue of the divider circuit, however, the measuring result fundamentally remains uninfluenced by changes in the intensity of the electromagnetic radiation to be analyzed.

As resistance tolerances in the resistor network of the programmable instrument amplifiers cannot be avoided, the result will be differences in the degree of amplification of the various instrument amplifiers. These differences may be determined by providing circuit elements in accordance with the invention ahead of each instrument amplifier to apply a gauging voltage to the inputs of the instrument amplifiers. These circuit elements are controlled by means of a third control circuit associated with them.

The gauging process substantially works as follows: First the amplification of the instrument amplifiers is programmed to the value 1 by means of the second control circuit. Subsequently the circuit elements apply to the inputs of the instrument amplifiers a gauging voltage of a value at which the subsequent components are balanced out in their dynamic range. The signal applied to the analog/digital converter then is digitalized and the information thus obtained is stored in a memory. In the subsequent steps the amplification always is adjusted to the next higher value and the procedure described above is repeated until all amplification stages have been covered. The resulting values stored and relating to each amplification stage then are set off as correcting factors against the respective measured values in accordance with the respective amplification stage adjusted. The offset furthermore may be determined by applying a gauging voltage of 0 volt value. The gauging procedure described also may take place during a current measuring process. Consequently all drifts are detected and the correction factors are updated accordingly.

In an especially preferred modification of the measuring assembly according to the invention the necessary gauging voltages are generated by means of digital-/analog converter. This affords the additional advantage of the possibility of applying a plurality of different voltage values to the input of the instrument amplifiers, whereby also the linearity behavior of the analog components can be determined. For example, a system test following the switch-on of the measuring system may reveal hidden errors within the analog circuit.

As explained above, rotary values of more than 90 degrees and thus ambiguities may be the result if the requirements as to resolution are high, simultaneously requiring a great measuring range. These ambiguities, however, still can be excluded by providing for at least two measurements according to the invention at different optical activities. Yet these measurements must not necessarily take place at the same time as is the case with the measuring arrangement described which includes a measuring beam path and a measuring range beam path. Instead, they may also be carried out one after the other. In this event, for example, the optical activity of the optically active element may be varied during two successive measurements. This may be obtained, for instance, by varying the pressure with circular voltage doubly refracting materials or by varying a magnetic or electrical field with media showing a magneto- or electro-optical effect.

In a preferred embodiment of this measuring assembly according to the invention at least two optically active elements having different optical activities are arranged on a rotating drum the axis of rotation of which extends parallel to the optical axis. The drum extends into the beam path exactly up to such a point that rotation of the drum will swing the optically active elements one after the other cyclically into the beam path. The motor driving the drum preferably is equipped with an angle pickup which in turn is connected electrically with the digital data processing means. Consequently the latter always is informed as to which optically active element happens to be in the beam path so that an exact coordination of the rotary value measured with the corresponding optically active element is warranted. Moreover, the drum mentioned or a structural member having the same function (e.g. linearly displaceable slide) also may comprise an area in which there is no optically active element. When this sector passes through the beam path, for instance, a void measurement may be made, in other words the entire system may be gauged.

In accordance with another modification of the measuring assembly according to the invention the optical activity is controlled by varying the layer length passed by the radiation to be analyzed. To this end a means is provided which consists of at least two optically active wedges arranged vertically in the beam path and being displaceable with respect to each other. One of the two wedges, for instance, is fixed, while the other one is supported movably. The total layer length thus may be varied homogeneously across the beam cross section by relative displacement of the wedges with respect to each other. Preferably this pair of wedges is made of quartz, the crystal axis thereof being oriented accordingly. The device mentioned not only has the advantage of excluding ambiguities in the measuring result by means of two subsequent measurements at different wedge positions. The fact that the overall layer length may be varied infinitely or in relatively fine steps always permits measurement in the range of the sine square transmission function of the analyzer in which range the rise and consequently also the resolution of the measuring result are the greatest.

As explained above, quartz is especially well suited as the optically active element. The layer length of the quartz must be very great if extremely high resolutions are to be obtained. However, especially natural quartz having the required purity over such a great layer length is rather expensive. To overcome this problem, the invention proposes to design the beam path by means of linear optics such that the optically active element or elements are passed several times by the electromagnetic radiation to be analyzed. During each cycle part of the radiation to be analyzed. During each cycle part of the radiation only is balanced out of the swing for detection, for example by means of a semitransparent mirror. The rotation of the polarization plane of that part of the radiation not balanced out, on the other hand, is increased by a constant amount during each cycle. On the whole, therefore, a characteristic means value of all portions of rotation is measured. This mean value of the individual portions of rotation may be coordinated exactly with a frequency value of the radiation to be analyzed in a manner corresponding to that of a certain discrete rotary value in accordance with the measuring assembly described above.

In accordance with a modification of the invention the measuring device is provided at the input end, e.g. in front of the entry surface of the linear polarizer with a means which permits an independent analysis regardless of the place and radiation characteristic of the radiation source. A diaphragm, a photoconductor, or other imaging elements, for example, may be used for this purpose. A diaphragm at the input end also may be designed as a slit in order to be able to mount the measuring device according to the invention, for instance, at the output of a monochromator.

The possibilities of application of the measuring assembly described above are not limited to the measurement of monochromatic radiation alone. In a special embodiment the measuring assembly according to the invention is provided with a device which permits passage only of a discrete frequency band of the electromagnetic radiation to be examined. Such devices may be, for example, screens or gratings or prisms or monochromators made of the same, acousto-optical filters or color or interference filters. Basically, these may be arranged at any desired point in the beam path. Especially the advantageous fact that always the optical center of gravity is determined with the instant measuring assembly, in combination with the monochromator means mentioned, permits spectral examinations to be made at a resolution and accuracy unknown so far.

In an especially preferred embodiment the above mentioned device consists of an interference course filter the spectral transmission properties of which are a function of the locus on the filter. This filter is arranged vertically with respect to the optical axis in the beam path, for example, being movable by a stepping motor.

In another embodiment the measuring assembly for determining the spectral characteristic of electromagnetic radiation is provided with a firmly disposed device with effects spectral decomposition of the radiation to be examined. Preferably this device is located in front of the analyzer and, for example, it may be a dispersing element (diffraction grating). The radiation to be analyzed thus is fanned spectrally and, for detection of the same, a plurality of photosensitive sensors are arranged in series. Thus a discrete frequency band is directed to each photosensitive sensor. The photosensitive sensors may be combined, for example, in the form of a photodiode array. Output signals of the individual photoelements are held in the usual manner by means of associated sample/hold circuits. The entire spectral characteristic of the radiation in this case is detected in real time because the optical centers of gravity are determined at the same time with a plurality of different frequency bands (as determined by the number of photodiodes).

Figure 1:
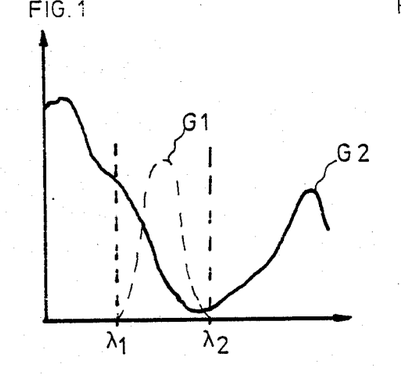
FIG. 1 shows the emission spectrum (intensity above frequency) of a first substance and the transmission function of an interference course filter at point X1.

In another special modification according to the invention the measuring assembly is provided with at least one sample space for spectrometric and/or photometric examinations of samples. Such a measuring assembly makes it possible to characterize pure substances and to analyze mixtures consisting of a great number of components. A suitable method called weighted spectral integration will be explained below for application of the measuring assembly described:

In FIG. 1 graph G2 shows the emission spectrum $I1(\lambda)$ of a first substance. Graph G1 in FIG. 1 describes the percentage transmission function $T(X1,\lambda)$ of an interference course filter point X1, which is any arbitrary point along the transmission path through the filter. filter at point X1 and subsequently passes through the first substance, a frequency band behind the same will be obtained which has the intensity distribution $I2(X1,\lambda)$. This relationship also may be described by the following formula:

$$I2(X1,\lambda) = T(X1,\lambda) \cdot I1(\lambda)$$

wherein:
$I1(\lambda)$: emission or absorption spectrum of the sample without filter
$T(X1,\lambda)$: transmission function of the interference course filter
$I2(X1,\lambda)$: intensity distribution behind the filter and interaction with the sample.

Figure 3A:
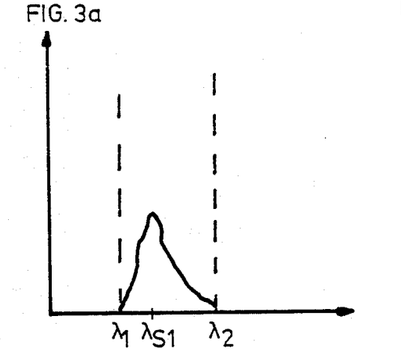
FIG. 3a shows the intensity distribution of the radiation downstream of the interference course filter and interaction with the first substance.

As an example FIG. 3a represents the intensity distribution $I2(X1,\lambda)$ following the first substance.

Figure 2:
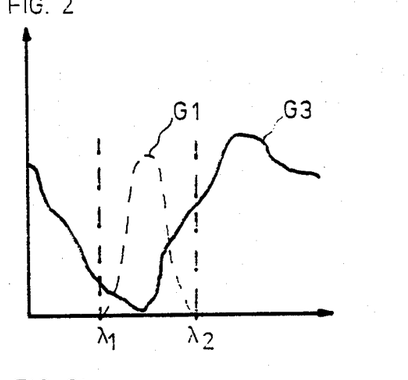
FIG. 2 shows a corresponding emission spectrum of a second substance.

Graph G3 in FIG. 2 shows the emission spectrum of a second substance. FIG. 2 also includes graph G1 which represents the percentage transmission function of the interference course filter at point X1. If the radiation transmitted by the interference course filter passes through the second substance, the intensity distribution obtained thus is that plotted in FIG. 3b.

Each substance thus presents a characteristic frequency distribution within a discrete frequency band. In an optically active element the individual frequencies transmitted of the radiation obtained and weighted with the optical rotation dispersion function f(I) contribute to the rotation of the plane of oscillation. The integrating effect of the photosensitive sensors thus provides the optical center of gravity:

$$\lambda_s = \int_{\lambda_1}^{\lambda_2} f(I2(X1,\lambda))a\lambda$$

Figure 3B:
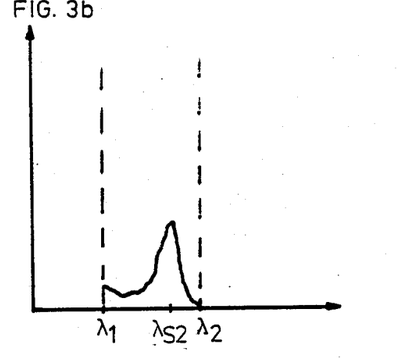
FIG. 3b shows a corresponding course upon interaction with the second substance.
Figure 3C:
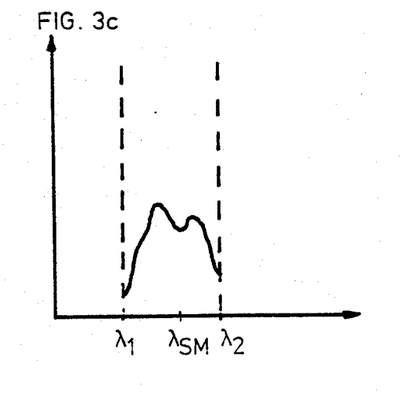
FIG. 3c shows the corresponding intensity distribution behind a mixture of first and second substances.

By illustration, therefore, the optical center of gravity $\lambda_{S1}$ of the first substance is approximately as plotted in FIG. 3a and the optical center of gravity $\lambda_{S2}$ of the second substance is approximately as shown in FIG. 3b. These magnitudes are determined by the measuring assembly according to the invention. If a mixture of the two substances is analyzed, of course, a characteristic intensity distribution will be obtained of the mixture as well, as shown for example in FIG. 3c. The optical center of gravity determined by the measuring assembly of the emission spectrum transmitted of the substance mixture is assumed to be $\lambda_{SM}$, this value lying between the optical center of gravity $\lambda_{S1}$ of the first substance and the optical center of gravity $\lambda_{S2}$ of the second substance. The standardized values of $\lambda_{S1}$ and $\lambda_{S2}$ with respect to $\lambda_{SM}$ then provide the mixing ratio of the two substances in the mixture. Of course, this applies only as long as no interactions take place between the substances, changing the emission spectrum. Any desired number of frequency bands may be selected of the spectrum emitted by the radiation source by using the interference course filter. If the mixture of substances contains more substances, more measurements at different frequency bands must be made in order to be able to determine their relationship of concentration. Consequently a system of equations is obtained in which each equation of the measuring series represents a filter position, i.e. the optical centers of gravities of the individual substances and the mixture of substances with this discrete frequency band. The number of equations corresponds to the number of different filter positions at which measurements must be made. In conclusion, the relationships of concentration of n substances in a mixture may be obtained by measurements at least $n-1$ filter positions, for example, by applying matrix calculation.

It is important that there be a linear relationship between the concentration C of the substance and the degree of modulation of the emission or absorption spectrum in order for the above considerations to be valid. The degree of modulation here always is understood as being the property of substances to change the spectrum emitted by the light source (frequency response of the intensity of the radiation absorbed or emitted by the sample). Furthermore, the concentration C must lie between the value Co=0 and the saturation concentration Cs, in other words the concentration at which the exciting spectrum undergoes maximum modulation specific of the substance.

In some cases, however, the above mentioned condition does not apply and, strictly speaking, it is applicable only in the event that the concentration is very low because together with the concentration also the intermolecular interactions rise and macroscopic charge patterns form which may change the emission or absorption spectrum.

Figure 4:
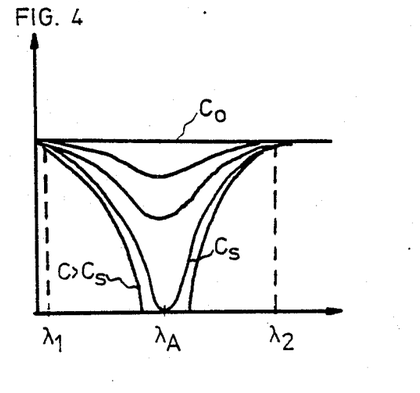
FIG. 4 shows the intensity distribution of the radiation emitted of a substance in response to the concentration thereof in the solvent, to explain the term used here of "degree of modulation"

The method according to the invention, namely multiple measurements made at different frequency bands, may be used also to determine the absolute concentrations of substances in a substance mixture where there is no linear relationship between the concentration and depth of modulation for such wide ranges of concentration (Co to Cs). In accordance with the invention, in this case the n spectra of a substance are determined at m different concentrations in the relevant range of concentrations. The individual concentrations preferably are so selected that a linear relation exists between the concentration and the degree of spectrum modulation in the $n-1$ intervals between them, within the limits of the measuring accuracy. FIG. 4 shows the example of the absorption spectrum of a substance at an absorption point ($\lambda_A$) at five different concentrations. If one takes a look at the spectrum in the interval ($\lambda_1$, $\lambda_A$) by means of the weighted spectral integration, the center of gravity wavelength determined will become displaced in the "direction" $\lambda_1$ as the concentration rises and toward $\lambda_2$ in the interval ($\lambda_A$, $\lambda_2$). This again shows that the frequency bands preferably are so selected that the weighted spectral integration is effected at flanks of the spectrum to be examined. It is there that the greatest resolution is obtained. If interpolations are made for each substance between m gauging concentrations, weighted spectral integrations have to be made at at least n.m frequency bands in analyzing a mixture of n substances.

In accordance with the claims a means is provided with the aid of which the exciting radiation intensity can be varied so that it may be found out whether Cs has been exceeded and, therefore, a solution for example must be diluted more. This, for example, may be a density glass which is swung into the beam path. If the emission spectrum does not change qualitatively at different radiation intensities, i.e. if the values $\lambda_S$ determined remain the same, the saturation concentration Cs has not yet been reached and consequently the measuring result is valid.

The band width transmitted, i.e. the outlet slit at the monochromator would have to be infinitely small in order to be able to draft such an equation system with the aid of a conventional monochromator in accordance with the method described above. The reason is that with the usual measuring arrangements for evaluation of the radiation transmitted by the monochromator, the integration always is unweighted across the entire band width, in other words only the intensity enters into the measuring result, the respective frequency shares remaining unconsidered. Consequently the method in combination with the measuring assembly according to the invention provides for substantial increase of the content of information of spectral examinations.

In this context it is a great advantage that the halfwave breadth in terms of frequency of the filter or monochromator does not influence the resolution of the method. Rather, the halfwave breadth of the filter always is to be as great as possible because, with a greater halfwave breadth, also the qualitative differences between two or more individual spectra are increased and consequently the optical centers of gravity determined by the measuring assembly show maximum differences. The individual frequency bands also may be overlapping, provided it is assured that the equations then obtained are independent also linearly. This may be obtained, for example, by means of a calculatory check run. A high value of the half width has the further advantage that the detectable limits may be broadened considerably, contrary to other methods of spectrum analysis which involve high losses of light.

In applications in which the type of substance is known from other measuring magnitudes, e.g. the retention time in chromatography and in which, furthermore, a change of the concentration of this substance has a linear influence on the modulation of the spectrum ray introduced, it is advantageous to dispense altogether with a limitation of the spectrum as effected by the filter. Thus it becomes possible to replace the integrators used in the field of chromatography which, as is known, determine the concentration by integrating a detector peak across the base width thereof. Then the relationship between the integral determined and the concentration of the substance must be known in order to provide an acceptable measuring accuracy. Yet this can be done only by complicated and expensive gauging procedures. These problems do not occur with a measuring assembly according to the invention because the integration automatically takes place across the detector peak because of the determination of the optical center of gravity. Consequently the accuracy achieved is much higher.

Fundamentally, solid, liquid, or gaseous substances may be analyzed by the measuring assembly described for the "weighted spectral integration", the sample chamber being designed accordingly to receive these substances.

When use is made of a novel method of analysis it may be advantageous to run a known method for control at the same time. To this end another preferred modification of the measuring assembly according to the invention for determining photometric magnitudes comprises a means in front of the sample space which constantly or temporarily balances out part of the radiation of the beam path. This partial beam may impinge on an associated photosensitive sensor, either directly or upon passing a second sample chamber which serves, for example, to receive a reference standard, the photosensitive sensor supplying a second reference signal. If the ratio is formed of the second reference signal and of the first reference signal obtained after the sample space, the function of a double beam photometer is fulfilled. Thus an additional adequate spectrophotometer is available which has a built-in wavelength gauging means. The photometric signal obtained as described above from the first reference signal also may be determined by a separate means, such as a beam splitter arranged downstream of the sample space. However, as this photometric signal and the first reference signal needed for determining the optical gravity of gravity are equal, it makes sense to obtain these signals from a common means.

In accordance with the invention it is also possible to combine two or more measuring assemblies or their functional groups for spectral and/or photometric analysis according to the invention in one apparatus. Then so-called reference samples may be arranged, for example, in the other beam paths so that a double beam spectrophotometer is available.

Fundamentally no mechanically movable parts are required in the course of measurement with the instant measuring assembly according to the invention. Instead, the measuring speed is determined only by the data collection time of the short time storages, i.e. the building-up times of the sample/hold elements. These times lie within a range of from 10 nsec to 15 $\mu$sec, depending on the required accuracy and price category. The analog signals, having been stored briefly, are digitalized and processed further by means of a digital data processing means, such as a microprocessor. Consequently the results of measurement are available directly, in other words in real time. It is especially for the analysis of pulsed electromagnetic radiation that the invention provides for a terminal by which the trigger input of the radiation source (e.g. pulse laser) may be connected to the output of the first control circuit associated with the short time storages. Thus the data entry cycle of the measuring assembly may be synchronized with the light source.

As explained before, the optical activity always is a function of the wavelength and of the temperature. The response to the wavelength is utilized in accordance with the invention for determining the wavelength of electromagnetic radiation. The temperature of the optically active element or elements must be known exactly if exact technical measuring statements are to be made. To this end it is provided in accordance with the invention that the temperature of the optically active element or elements is detected by at least one thermosensitive sensor which is electrically connected to the digital data processing means. Accordingly, the measuring result may be corrected by the actual value of the temperature. Exact knowledge of the temperature response of the optically active element used is necessary if the correction mentioned above is to be made accurately. If this temperature response is unknown, preferably a means, such as a Peltier element is provided to bring the optically active element or elements to the desired temperature.

BRIEF DESCRIPTION OF THE DRAWINGS

The invention will be described further, by way of example, with reference to the accompanying drawings, in which.

WAYS OF CARRYING INTO EFFECT THE INVENTION

Figure 5:
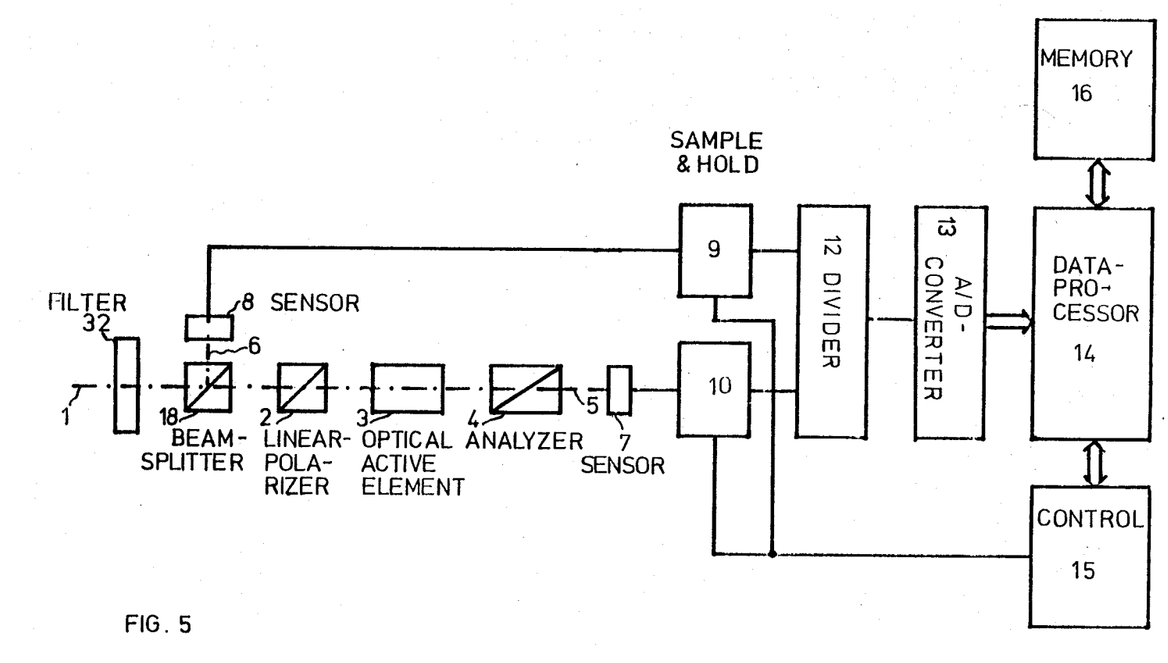
FIG. 5 is a diagrammatic sketch of a measuring assembly according to a first embodiment of the invention.

FIG. 5 is a diagrammatic presentation of a first embodiment of the invention. It shows in succession on the optical axis of the electromagnetic radiation 1 to be examined a filter 32, a means 18, especially a beam splitter for balancing out the first reference signal, a linear polarizer 2, a quartz serving as optically active element 3, and an analyzer 4. The partial beam 6 which is balanced out for determining the first reference signal impinges on a first photosensitive sensor 8, and the radiation 5 coming from the analyzer 4 is incident upon a second photosensitive sensor 7. The signal outputs of the two photosensitive sensors 7, 8 each are connected by a sample/hold circuit 9, 10 (here being short time storages) to the inputs of a divider circuit 12. The short time storages 9,10 are controlled in synchronism by means of a first control circuit 15 connected at the input end to a digital data processing means 14. The output of the divider circuit 12 is connected to the input of an A/D converter 13 for purposes of digitalizing the measuring signals, the converter in turn being connected at the output end to the digital data processing means 14. The digital data processing means 14 is connected to a memory 16 for comparing the measuring results determined with the ORD spectrum of the optically active element 3 used. The above mentioned memory 16 stores the characteristic features of the optically active element 3, in this case a quartz.

Figure 6:
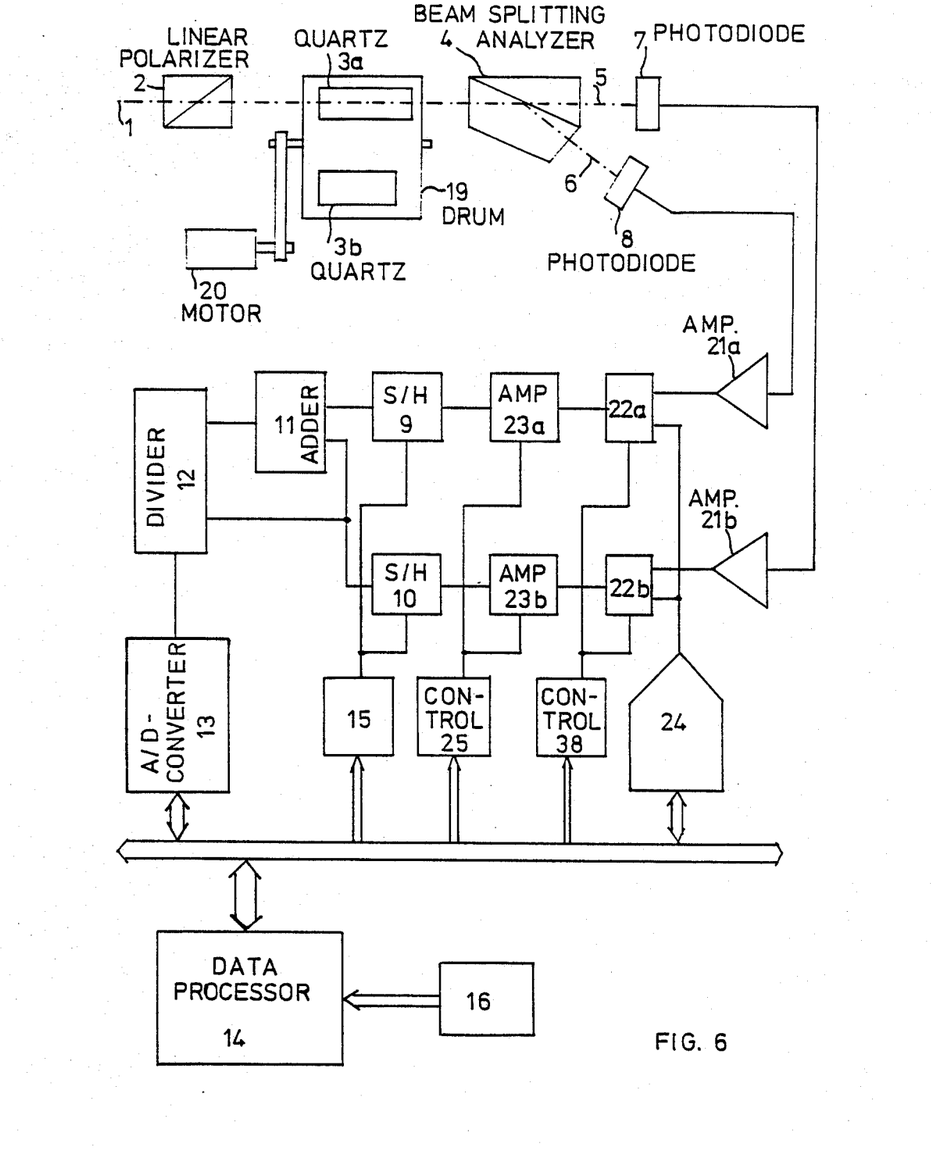
FIG. 6 is a basic circuit diagram of the measuring assembly according to the invention with an enlarged measuring range.

FIG. 6 shows an embodiment of the invention with which an enlargement of the measuring range has been realized. To this end a drum 19 is arranged in the beam path 1 between the linear polarizer 2 and the analyzer 4, two quartzes 3a, 3b having different layer lengths being disposed in said drum. The drum 19 is driven by a motor 20 so that the optically active elements 3a, 3b may be swung cyclically one after the other into the beam path 1. The analyzer 4 in this case consists of a beam splitting analyzer. As already explained, therefore, the first reference signal is obtained of the sum of the ordinary and extraordinary partial beams exiting from the beam splitting analyzer 4.

As regards the nature of the beam splitting analyzer, with most polarization double or multiple prisms the degree of polarization of both partial beams is sufficient, yet the angle of divergence between these components depends on the wavelength of the electromagnetic radiation impinging on the beam splitter. Consequently the position of the photo-detectors always should be adapted to the respective wavelength. For this reason it is preferred to use a so-called Foster polarizer as the beam splitting analyzer with which one of the two components is deflected because of total reflection at the cement layer or at the gap between the two polarizer prisms. In this manner the angle of divergence is independent of the wavelength with this type of polarizer.

Photodiodes 7, 8 are positioned in the beam paths of the two partial beams 5, 6 to detect the intensities thereof. The signal outputs of these photodiodes are connected by way of input operation amplifiers 21a, 21b to a respective input of a circuit means 22a, 22b. The outputs of the circuit means which are controlled by an associated third control circuit 38 are passed on to the inputs of instrument amplifiers 23a, 23b which again are connected at the output end to the inputs of sample/hold circuits 9, 10 (short time storages). The outputs of the short time storages 9 and 10, respectively, further are connected to the inputs of an adder circuit 11. The output signal of the adder circuit 11 is applied to the dividend input of a divider circuit 12. In accordance with the embodiment shown in FIG. 6 the divisor input of the divider circuit 12 is connected to the output of the short time storage 10 associated with the extraordinary partial beam 5. For further processing of the output signal of the divider circuit 12 the latter is followed by an A/D converter 13 and a digital data processing means 14, as is the case with the measuring assembly shown in FIG. 5. Selectively, gauging voltages may be connected to the inputs of the instrument amplifiers 23a, 23b by the circuit means 22a, 22b. The gauging voltages preferably are generated by a digital/analog converter. A second control circuit 25 is associated with the programmable instrument amplifiers to adjust the amplification, and it in turn is connected to the digital data processing means 14.

Figure 7:
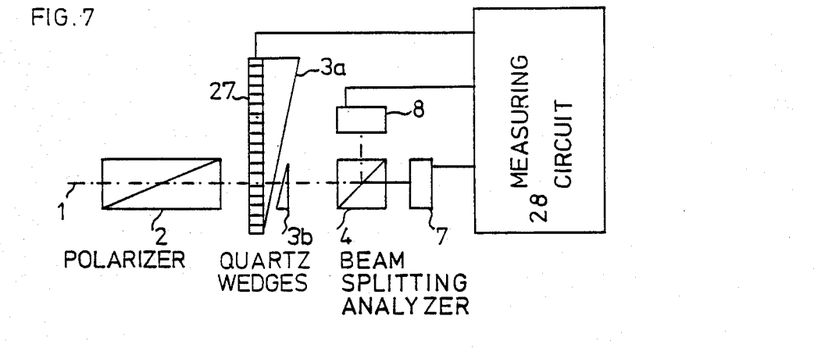
FIG. 7 shows another embodiment of the measuring assembly according to the invention with which the optically active element consists of a pair of quartz wedges which are displaceable in opposite sense.

FIG. 7 shows another embodiment of the measuring assembly according to the invention with which the optically active element consists of a pair of quartz wedges which are displaceable in opposite sense. The electromagnetic radiation 1 to be analyzed passes through a Glan Thompson polarizer 2, a large quartz wedge 3a which is arranged for movement vertically with respect to the optical axis and coupled to a path pickup 27, another small quartz wedge 3b, and subsequently impinges on a Glan Taylor polarizer 4 serving as beam splitting analyzer. The two radiation components polarized vertically with respect to each other of the Glan Taylor polarizer are detected by photodetectors 7, 8 associated with them and connected at the output end to a measuring circuit 28 for the further processing of the signals measured. The path pickup 27 is connected to the digital data processing means for control of the position of the big quartz 3a.

Figure 8:
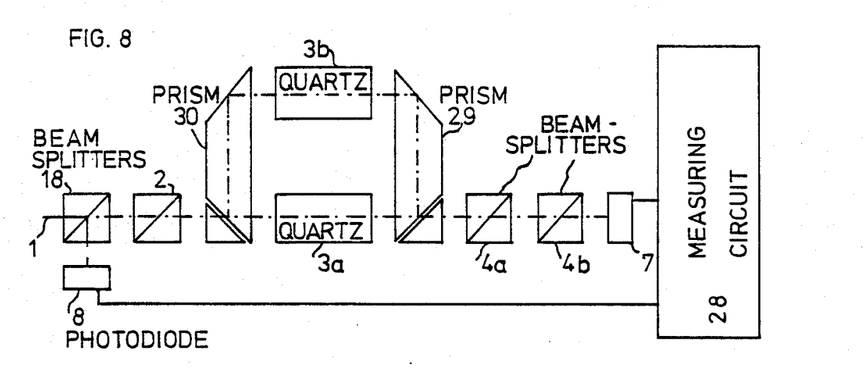
FIG. 8 shows another embodiment of the measuring assembly according to the invention with which the optically active element or elements are passed several times by the radiation.

A special embodiment of the invention suitable for applications in which the requirements as to resolution are high, up to the Zeeman effect is shown in FIG. 8. Here the radiation 1 to be analyzed passes several times through two optically active elements 3a, 3b consisting of an R-quartz and an L-quartz. The beam path is guided by two Dove-like prisms 29, 30, the mean cycling time of all rotary portions being determined by the degree of reflection of the semitransparent layer at the point of reversion of the Dove prism 29. The polarizer means 18, 2, 4a, and 4b preferably are simple dielectric beam splitting cubes. The radiation transmitted by the analyzer 4a, 4b as well as the partial beam diverted by the beam splitter 18 to provide the first reference signal are detected by their corresponding photodiodes. The photodiodes also are connected to a measuring circuit 28 for further evaluation of the signals.

Figure 9:
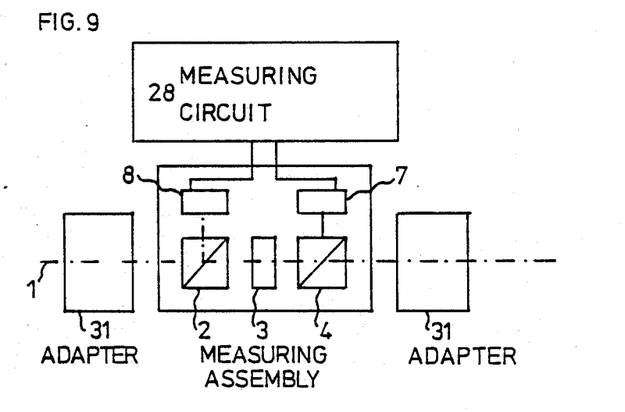
FIG. 9 shows an embodiment of the measuring assembly for simple wavelength and energy determination at or in glass fiber nets.

FIG. 9 describes a modification of the measuring assembly for simple wavelength and energy determination at or in networks based on optical fibers. The radiation to be analyzed in this case passes through a beam splitting polarizer 2, a quartz plate 3, and a beam splitting analyzer 4. The partial beams which are diverted by the beam splitters impinge on associated photoreceptors 7, 8 the partial beam balanced out by the beam splitting polarizer 2 corresponding to the reference signal, and the partial beam balanced out by the beam splitting analyzer 4 corresponding to the signal which is responsive to the wavelength. For easier integration of the measuring assembly described in glass fiber nets, it is furnished at the input and output ends with adapters 31 customary in the industry.

Figure 10:
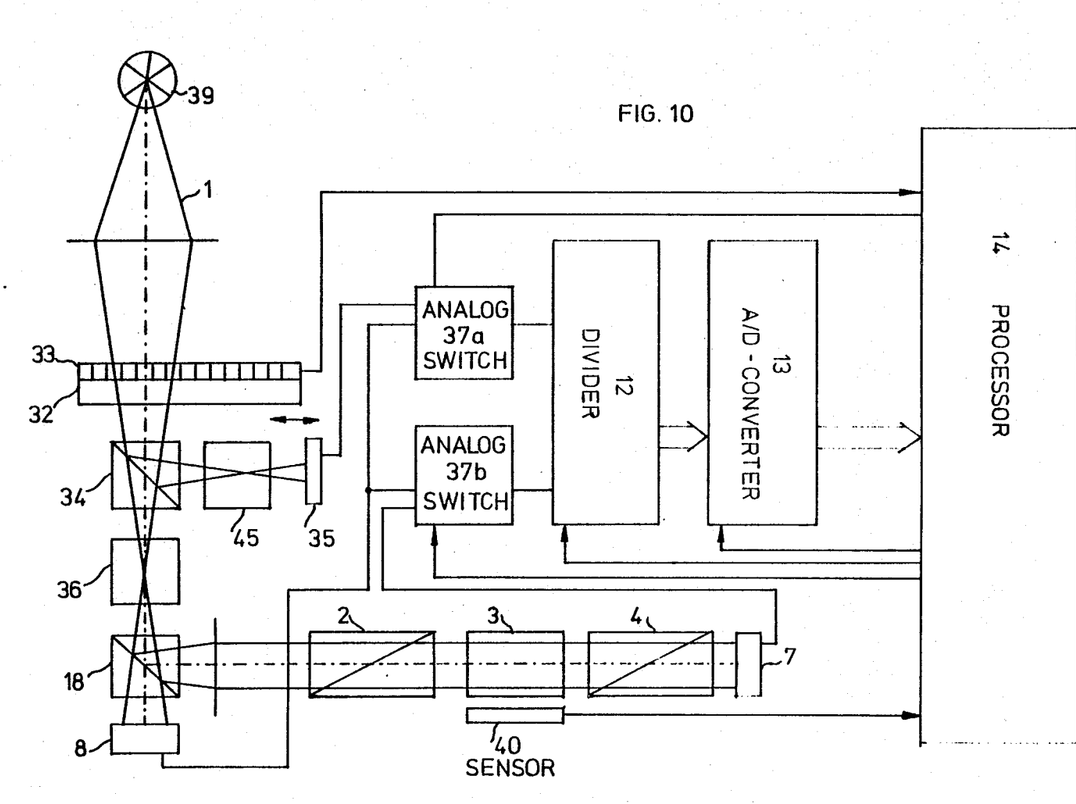
FIG. 10 shows another embodiment of a measuring assembly according to the invention for the combined weighted spectral integration and spectral photometric analysis of a sample.

A preferred arrangement for the combined weighted spectral integration and spectrophotometric analysis of a sample is shown in FIG. 10. The radiation 1 emitted by a light source 39 passes through an interference course filter 32 arranged for movement vertically with respect to the beam path, a first beam splitter 34, the sample 36 to be examined, and a second beam splitter 18. Photodiodes 35, 8 are provided as detectors in one each of the partial beams of the two beam splitters 34 and 18. A second sample chamber receiving a reference standard 45 is arranged upstream of the photodiode 35 which is coordinated with the partial beam neutralized by the first beam splitter 34. The output signal of the photodiode 35 associated with the first beam splitter 34 in this case corresponds to the second reference signal, while the output signal of the photodiode 8 associated with the second beam splitter 18 corresponds to the first reference signal. Photometric magnitudes which may be associated with the sample may be calculated based on the relationship of the two signals. The other partial beam of the second beam splitter 18 further passes through a linear polarizer 2, a quartz 3, an analyzer 4, and finally impinges on a photodiode 7 for determining the signal which is responsive to the wavelength. The ratio of this signal to the first reference signal then serves for spectrometric evaluation of the radiation. The signal outputs of the photodiodes 35 and 8 and of the photodiodes 8 and 7 are selectively applied to the inputs of a divider circuit 12 by means of analog switches 37a, 37b in order to make the measuring assembly simpler. For further evaluation of the measuring signals obtained, the divider circuit 12 is connected by an analog/digital converter 13 to a microprocessor system 14. This permits selection between the determination of photometric magnitudes and a weighted spectral integration. The interference course filter 32 is coupled to a path pickup 33 which in turn is connected to the microprocessor system, so as to be able to control the position of this filter. Accurate measuring results are assured by the fact that a temperature sensitive sensor likewise is connected electrically to the microprocessor system.

Figure 11:
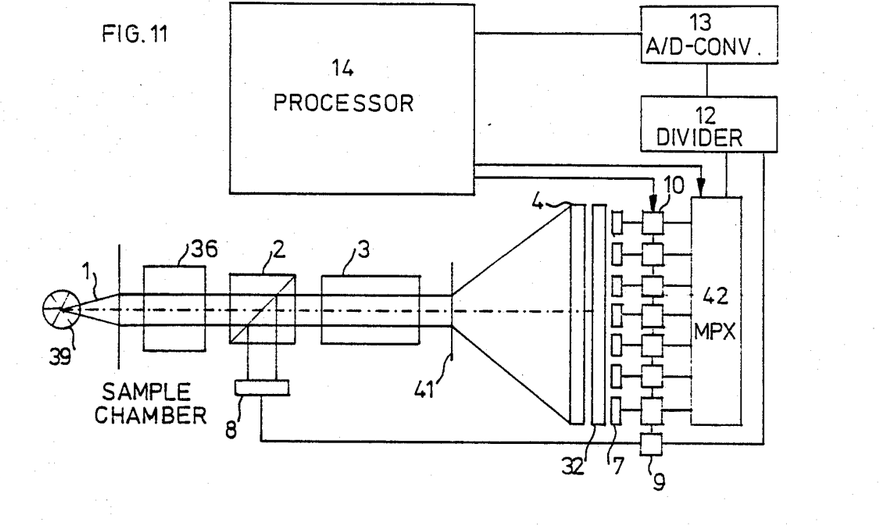
FIG. 11 shows an embodiment of a measuring assembly according to the invention for the spectral photometric analysis of samples in real time.

FIG. 11 shows another embodiment according to the invention which is suitable in general for the real time spectrum analysis of electromagnetic radiation. A sample space is located between the radiation source and the linear polarizer especially for the spectrophotometric examination of substances. The radiation 1 emitted by the light source 39 passes through the sample chamber 36 where it is changed as to its frequency spectrum in response to the substance or mixture of substances, and then continues to pass through the linear polarizer 2, an optically active element 3 and finally reaches the analyzer 4 through a lens 41. The lens 41, for example a cylindrical lens or a corresponding glass fiber optic serves the purpose of widening the light beam bundle. Any lens errors in this case are constant and thus may be compensated. Leaving the analyzer 4, the radiation 1 finally reaches a so-called photodiode array 7 by way of an interference course filter 32 which in this case is fixed and not movable. The transmission function of this filter 32 differs in response to the point of incidence of the radiation 1 on the filter 32. Consequently a respective defined discrete frequency band of the radiation 1 reaches each element of the photodiode array 7. The outputs of the individual photodiodes of the array 7 are connected to a sample/hold circuit 10 the signal outputs of which are applied to the inputs of a multiplexer 42 which in turn is connected at its output end to an input of the divider circuit 12. The reference signal in this case is obtained from the neutralized partial beam of the linear polarizer 2. A photosensitive sensor 8 is disposed in this partial beam and the signal output thereof is applied through a sample/hold circuit 9 to the other input of the divider circuit 12. As before, the output of the divider circuit 12 is connected to the input of an A/D converter 13. The latter in turn is connected to a microprocessor system 14 in which the entire control and evaluation of the measuring signals take place.

The delays in time caused with the measuring assembly shown in FIG. 10 by the fact that the optical centers of gravity are determined one after the other at different positions of the interference course filter, i.e. frequency bands do not occur with the measuring assembly just described because here the values measured are detected simultaneously at different frequency bands. For simplification of the measuring assembly, the measuring signals stored in the sample/hold circuits 9 and 10 are applied successively by means of the multiplexer 42 to the further processing. The use of corresponding quick microprocessors as already on the market has the consequence that the delay in time caused by the successive processing of the measuring signals stored in the sample/hold circuit 10 hardly has any influence at all. The ratios of concentration of the individual substances in the mixture of substances of the sample 36, therefore, practically are determined in real time. Because of this the measuring assembly just described is especially well suited for on-line process control in chemical processing engineering. Again it is advantageous that no intervention is required in the chemical production or control circuit, in other words no sample is taken from the circulation as must be done, for instance, in chromatography.

Figure 12:
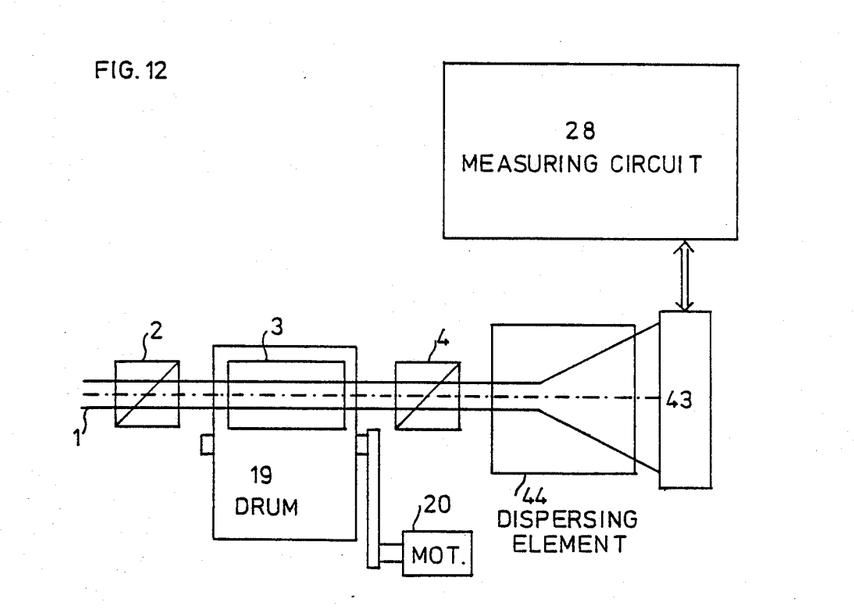
FIG. 12 shows another embodiment of a measuring assembly according to the invention for the real time spectrum analysis of electromagnetic radiation.

FIG. 12 shows another embodiment of the measuring assembly for the simultaneous detection of the optical centers of gravity with different frequency bands. This embodiment also is destined quite generally for the analysis of electromagnetic radiation in respect of their spectral characteristic. The radiation, for instance, already may have passed a sample. The radiation 1 to be analyzed passes through the linear polarizer 2, the optically active element 3, and the analyzer 4. Furthermore, the radiation 1 reaches a dispersing element 44 which, for example, is a diffraction grating, a prism, or an acousto-optical filter. An acousto-optical filter is a commercially available structural element which changes the angle of diffraction and consequently the frequency band of the radiation transmitted in response to an externally applied acoustic excitation wave. The spectrum of the light radiation incident on the filter thus may be scanned by varying the excitation frequency.

The radiation 1 which is fanned up by means of the dispersing element subsequently impinges on a CCD line 43. Thus each cell unit of the CCD line receives a discrete frequency band of the radiation 1, in the same manner as in the case of the embodiment shown in FIG. 11. CCD lines are commercially available structural elements which are used, for example, for detection in video cameras. The data stored by way of charge carriers, here the measuring values at different frequency bands, then may be read sequentially. The CCD line is connected to the input of a measuring circuit 28 for further processing of these signals. The optically active element 3 in the measuring assembly described above may be moved out of and into the beam path 11, in this case for example by a rotatable drum 19. This swinging out serves to provide the reference signal, in other words a void measurement is carried out with the intensity values detected in the CCD line and associated with the individual frequency bands being stored in the measuring circuit 28 as reference values. The intensity values then detected by each element of the CCD line 43 upon passage of the optically active element 3 each are standardized in respect of their corresponding reference values stored in the measuring circuit 28. Consequently a separately reference value is associated with each element of the CCD line 43 so that even considerable differences in intensity across the cross section of the radiation 1 have no influence on the measuring accuracy.

What is claimed is:

1. A measuring assembly for analyzing a beam of electromagnetic radiation across a measuring range to determine the wavelength center of gravity thereof, comprising:
    (a) a linear polarizer interposed in the path of said beam, said polarizer having a first predetermined polarization direction;
    (b) at least two optically active elements interposed in the path of said beam, each of said elements having a different and known optical activity; one of said optically active elements having a rotary value, with respect to the polarized radiation, not exceeding 90 degrees across the measuring range; another of said optically active elements having a rotary value, with respect to the polarized radiation, exceeding 90 degrees across the measuring range;
    (c) an optical analyzer having a second predetermined polarization direction with respect to said first predetermined polarization direction, said analyzer being interposed in the path of said beam after said beam has passed through said linear polarizer and at least one of said optically active elements, said analyzer having an exit side for passing said beam;
    (d) a first photosensitive sensor interposed in the path of said beam after said beam has passed through said analyzer;
    (e) means for obtaining a reference beam, said means located before the exit side of said analyzer;
    (f) a second photosensitive sensor positioned to receive said reference beam; and
    (g) a measuring circuit comprising:
        (i) a divider circuit having inputs respectively connected to said first and second photosensitive sensors;
        (ii) an analog-to-digital converter connected to said divider circuit; and
        (iii) a digital data processor connected to said analog converter, said data processor having a memory means for prestoring optical rotation dispersion data relating to said optically active elements, and means for calculating the wavelength center of gravity of said beam of electromagnetic radiation.

2. The apparatus of claim 1, wherein said means for obtaining a reference beam further comprises a beam splitter positioned ahead of said analyzer.

3. The apparatus of claim 1, wherein said optical analyzer comprises a polarized beam splitter having included therein said means for obtaining a reference beam.

4. The measuring assembly of claim 3, wherein said measuring circuit further comprises a first short time storage connected to receive said first photosensitive sensor signals; a second short time storage connected to receive said second photosensitive sensor signals; a control circuit connected to said first short time storage and to said second short time storage in order to control synchronously the first and second short time storage; an adder circuit connected with its inputs to said first and second short time storage and connected with its output to one input of said divider circuit, having connected its other input directly to one of the short time storages.

5. The apparatus of claim 4, wherein said measuring circuit further comprises a first and second programmable amplifier respectively coupled upstream of said first and second short time shortages and means for switching a calibration voltage to the inputs of said first and second programmable amplifier.

6. The apparatus of claim 1, wherein said optically active elements are mounted on a rotatable drum, said drum is rotatable about an axis parallel to said beam, each of said optically active element being swung subsequently into the path of said beam.

7. The apparatus of claim 1, further comprising means for directing said beam of electromagnetic radiation through said optically active elements more than one time.

8. The apparatus of claim 1, further comprising a filter interposed in the path of said beam, said filter having means for permitting passage of a discrete frequency band of said electromagnetic radiation.

9. The apparatus of claim 1, further comprising a dispersing element for spectrally decomposing the radiation, said dispersing element being arranged in the beam path before the first and second photosensitive sensor.

10. The apparatus of claim 1, further comprising a test sample interposed in the path of said beam before said analyzer.

11. The apparatus of claim 10, further comprising a beam splitter interposed in the path of said beam before said sample, said beam splitter having means for providing a secondary reference beam.

12. The apparatus of claim 1, wherein said at least two optically active elements are positioned to simultaneously pass said beam.

13. The apparatus of claim 1, wherein said at least two optically active elements are positioned to sequentially pass said beam.

* * * * *

UNITED STATES PATENT AND TRADEMARK OFFICE
CERTIFICATE OF CORRECTION

PATENT NO. : 4,822,169

DATED : April 18, 1989

INVENTOR(S) : Richard Distl, Ulrich Schmidt

It is certified that error appears in the above-identified patent and that said Letters Patent is hereby corrected as shown below:

In column 2, line 16, "characteristics" should be -- characteristic --.

In column 4, line 53, "$A=A_O \cdot \cos^2 \cdot C$" should be -- $A=A_O \cdot \cos^2 \alpha \cdot C$ --.

In column 7, line 58, "eather" should be -- rather --.

In column 11, lines 28-29, delete "to be analyzed. During each cycle part of the radiation"; in column 11, line 36, "means" should be -- mean --.

In column 12, line 10, "with" should be -- which --; in

In column 21, line 23, "separately" should be -- separate --.

Signed and Sealed this

Sixteenth Day of January, 1990

Attest:

JEFFREY M. SAMUELS

*Attesting Officer*  *Acting Commissioner of Patents and Trademarks*